(12) United States Patent
Goel et al.

(10) Patent No.: US 7,566,359 B2
(45) Date of Patent: Jul. 28, 2009

(54) ULTRAVIOLET LAMP WITH ABSORPTIVE BARRIER

(75) Inventors: Rakesh Goel, Irving, TX (US); Ammar Kailani, Richardson, TX (US)

(73) Assignee: Lennox Manufacturing Inc., Richardson, TX (US)

( * ) Notice: Subject to any disclaimer, the term of this patent is extended or adjusted under 35 U.S.C. 154(b) by 298 days.

(21) Appl. No.: 11/557,334

(22) Filed: Nov. 7, 2006

(65) Prior Publication Data

US 2008/0121823 A1 May 29, 2008

(51) Int. Cl.
*B01D 39/00* (2006.01)
*A61L 2/08* (2006.01)
*G01J 1/32* (2006.01)

(52) U.S. Cl. ............................. 96/224; 422/24; 250/205
(58) Field of Classification Search .................. 250/205; 422/24; 96/224
See application file for complete search history.

(56) References Cited

U.S. PATENT DOCUMENTS

| 1,746,024 | A | | 2/1930 | Brandt, Sr. | |
|---|---|---|---|---|---|
| 3,745,750 | A | | 7/1973 | Arff | |
| 3,804,942 | A | * | 4/1974 | Takahashi et al. | 423/239.1 |
| 3,995,191 | A | * | 11/1976 | Kaduk et al. | 313/485 |
| 4,088,802 | A | * | 5/1978 | Shriver, Jr. | 427/67 |
| 4,701,195 | A | * | 10/1987 | Rosendall | 96/136 |
| 5,078,971 | A | * | 1/1992 | Matuda et al. | 422/121 |
| 5,288,231 | A | | 2/1994 | Kuehn et al. | |
| 5,997,619 | A | * | 12/1999 | Knuth et al. | 96/224 |
| 6,143,047 | A | * | 11/2000 | Jodoin et al. | 55/323 |
| 6,730,265 | B2 | * | 5/2004 | Horton, III | 422/24 |
| 6,869,468 | B2 | * | 3/2005 | Gibson | 96/224 |
| 6,984,259 | B2 | | 1/2006 | Hurst | |
| 7,020,417 | B2 | * | 3/2006 | Nomura et al. | 399/111 |
| 2004/0101327 | A1 | * | 5/2004 | Nomura et al. | 399/111 |
| 2005/0013729 | A1 | | 1/2005 | Brown-Skrobot et al. | 422/24 |
| 2005/0016543 | A1 | * | 1/2005 | Geist | 128/207.14 |
| 2005/0061656 | A1 | | 3/2005 | Benoit et al. | |
| 2007/0284687 | A1 | * | 12/2007 | Rantala | 257/432 |

* cited by examiner

*Primary Examiner*—Walter D Griffin
*Assistant Examiner*—Amber Orlando

(57) ABSTRACT

A heating, ventilating and air conditioning (HVAC) system, comprising a heat exchanger plenum having a surface located therein that is susceptible to degradation upon exposure to light, and a light bulb located within the plenum. In one embodiment, the light bulb has a side directed toward the surface and a light-absorptive barrier coupled to the side. The light-absorptive barrier is configured to reduce direct light transmission from the light bulb to the surface to thereby inhibit degradation of the surface. The invention further provides an HVAC system comprising a light bulb configured to emit photonic energy, and an absorptive barrier coupled to at least a portion of an outside of the bulb. The absorptive barrier is configured to substantially reduce transmission of the emitted photonic energy beyond the portion of the bulb.

27 Claims, 4 Drawing Sheets

ULTRAVIOLET LAMP WITH ABSORPTIVE BARRIER

TECHNICAL FIELD OF THE INVENTION

The present invention is directed, in general, to ultraviolet lamps and, more particularly, to an absorptive barrier to prevent transmission of ultraviolet light within a designated region of an ultraviolet light source.

BACKGROUND OF THE INVENTION

Indoor air can include trace amounts of contaminants: e.g., dust, smoke, carbon monoxide, as well as volatile organic compounds generated or outgassed from the living space as a byproduct of our modern building methods. Particular offenders among these are the adhesives used for installation of carpets, flooring, insulation, etc. As indoor air flows through the return ducts of a heating, ventilation and air conditioning (HVAC) system, the air first encounters the system air filter which blocks the passage of particulate contaminants, and allows the return air to enter the portion of the HVAC system where it is heated, cooled, humidified, or dehumidified. A drawback to employing filters is that they simply block the passage of particulate contaminants and do not destroy them. However, they are essential in removing particulate contaminants from the air prior to conditioning.

It is known to use ultraviolet (UV) radiation alone in HVAC systems to kill airborne bacteria and viruses. Additionally, photocatalytic oxidation (PCO) air purification systems employ a photocatalytic coating, e.g., titanium dioxide, in combination with an activating photonic light source of a particular wavelength to destroy indoor airborne contaminants including volatile organic compounds such as formaldehyde, toluene, propanal, butene, and acetaldehyde. The system arrangement commonly includes one or more ultraviolet lamps, and a photocatalytic monolith, such as a honeycomb, coated with the photocatalytic coating. Titanium dioxide is well known as a photocatalyst in a fluid purifier to destroy such contaminants. When the titanium dioxide is illuminated with UV light, photons are absorbed by the titanium dioxide, promoting an electron from the valence band to the conduction band, thus producing a hole in the valence band and adding an electron in the conduction band. The promoted electron reacts with oxygen, and the hole remaining in the valence band reacts with water, forming reactive hydroxyl radicals. When a contaminant adsorbs onto the titanium dioxide photocatalyst, the hydroxyl radicals attack and oxidize the contaminants to water, carbon dioxide, and other substances.

UV lamps in PCO applications are customarily tubular in form, and emit ultraviolet-wavelength photons within 360° around the longitudinal axis of the lamps. While UV light is extremely useful in the air purification and PCO applications, UV light is also very harmful to certain materials commonly found in the HVAC system, e.g., the air filter, electrical insulation, other polymers, etc. Exposure of these components to UV radiation results in early degradation and decreased system performance.

Accordingly, what is needed in the art is a device that protects vulnerable system components from UV light while not interfering in the air purification and PCO applications.

SUMMARY OF THE INVENTION

To address the above-discussed deficiencies of the prior art, the present invention provides, in one aspect, a heating, ventilating and air conditioning (HVAC) system, comprising a heat exchanger plenum having a surface located therein that is susceptible to degradation upon exposure to light, and a light bulb located within the plenum. In one embodiment, the light bulb has a side directed toward the surface and a light-absorptive barrier coupled to the side. The light-absorptive barrier is configured to reduce direct light transmission from the light bulb to the surface to thereby inhibit degradation of the surface. The invention further provides an HVAC system comprising a light bulb configured to emit photonic energy, and an absorptive barrier coupled to at least a portion of an outside of the bulb. The absorptive barrier is configured to substantially reduce transmission of the emitted photonic energy beyond the portion of the bulb.

The foregoing has outlined features of the present invention so that those skilled in the pertinent art may better understand the detailed description of the invention that follows. Additional features of the invention will be described hereinafter that form the subject of the claims of the invention. Those skilled in the pertinent art should appreciate that they can readily use the disclosed conception and specific embodiment as a basis for designing or modifying other structures for carrying out the same purposes of the present invention. Those skilled in the pertinent art should also realize that such equivalent constructions do not depart from the spirit and scope of the invention.

BRIEF DESCRIPTION OF THE DRAWINGS

For a more complete understanding of the invention, reference is now made to the following descriptions taken in conjunction with the accompanying drawing, in which.

DETAILED DESCRIPTION

Figure 1:
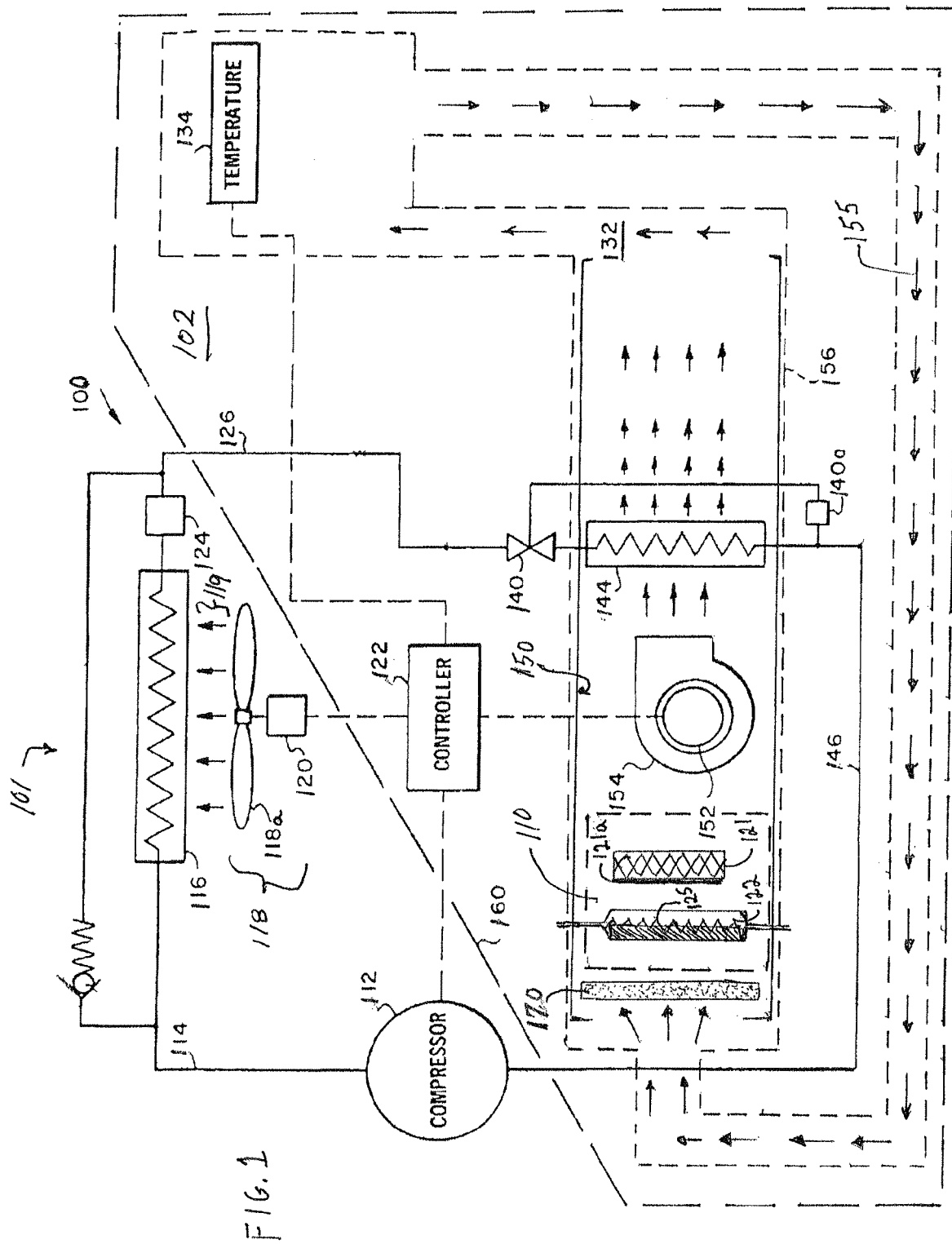
FIG. 1 illustrates a schematic view of a conventional heating, ventilation and air conditioning (HVAC) system having a photocatalytic oxidation (PCO) subsystem and constructed according to the principles of the present invention.

Referring initially to FIG. 1, illustrated is a schematic view of a conventional heating, ventilation and air conditioning (HVAC) system 100 having a photocatalytic oxidation (PCO) subsystem 110 and constructed according to the principles of the present invention. The photocatalytic oxidation (PCO) subsystem 110 may also be considered to be an air purifier. The HVAC system 100 comprises an outdoor portion 101, i.e., above line 160, and an indoor portion 102, i.e., below line 160. The outdoor portion 101 comprises a conventional electric motor-driven compressor 112 connected via a conduit 114 to a heat exchanger 116 disposed outdoors, typically, and comprising a refrigerant fluid primary condenser 116. In the embodiment illustrated in FIG. 1, heat exchange between refrigerant fluid flowing through the condenser heat exchanger 116 and ambient air 119 is controlled by a fan 118 having plural fixed-pitch blades 118a and which is driven by a variable speed electric motor 120. The electric motor 120 may be an electrically-commutated type operating on variable frequency and voltage AC electric power as supplied to the motor via a suitable controller 122. Fan 118 propels a heat exchange medium, such as ambient outdoor air 119, through the condenser heat exchanger 116 in a known manner. The condenser heat exchanger 116 may also operate with other forms of heat exchange media at controlled flow rates thereof. Control of heat exchange medium 119 flowing over condenser heat exchanger 116 may take other forms such as a constant speed variable pitch fan, air flow control louvers, or control of a variable flow of a liquid heat exchange medium. The condenser heat exchanger 116 is also operably connected to a conventional refrigerant fluid filter and dryer 124 disposed in a conduit 126 for conducting condensed refrigerant fluid to a conventional refrigerant fluid expansion device 140. A temperature sensor 134, disposed within a conditioned space 132 to be conditioned by the system 100, is also operably connected to the controller 122. Controlled/conditioned space 132, as well as a return air path 155 from space 132, are represented schematically in the drawing figures.

The indoor portion 102 comprises the controller 122, a heat exchanger plenum 150, a system filter 170, the photocatalytic oxidation subsystem 110, a drive motor 152, a motor-driven blower 154, the refrigerant fluid expansion device 140, a heat exchanger 144, and the temperature sensor 134. While this discussion is directed to a photocatalytic oxidation subsystem, the conditions are substantially the same as for those installations wherein only a UV lamp is used to kill bacteria and viruses without benefit of a photocatalyst. Conduit 126 is operable to deliver refrigerant fluid to the conventional refrigerant fluid expansion device 140 and to the heat exchanger 144 or so called evaporator 144, respectively. The expansion device 140 includes a remote temperature sensor 140a which is adapted to sense the temperature of refrigerant fluid leaving the heat exchanger 144 by way of a conduit 146. Conduit 146 is commonly known as the suction line leading to the compressor 112 whereby refrigerant fluid in vapor form is compressed and recirculated through the system 100 by way of condenser heat exchanger 116. Heat exchangers 116, 144 may be conventional multiple fin and tube type devices, for example. One who is of skill in the art will understand the functioning of the HVAC heretofore described.

The PCO subsystem 110, within the heat exchanger plenum 150, comprises a photocatalytic monolith 121, a photocatalytic coating 121a, and a photocatalytic light bulb 122. The PCO subsystem 110 may comprise one or more ultraviolet lamps having an electrical circuit 125 therein, and the photocatalytic monolith 121, such as a honeycomb, may have a titanium dioxide coating 121a. In one embodiment, the photocatalytic light bulb 122 may comprise a UV light bulb. In a preferred embodiment, the photocatalytic light bulb 122 emits photons of a particular wavelength to cause the photons to be absorbed by the titanium dioxide coating 121a, promoting an electron from the valence band to the conduction band, thus producing a hole in the valence band and adding an electron in the conduction band. The promoted electron reacts with oxygen, and the hole remaining in the valence band reacts with water, forming reactive hydroxyl radicals. When a contaminant adsorbs onto the titanium dioxide photocatalyst, the hydroxyl radicals attack and oxidize the contaminants to water, carbon dioxide, and other substances.

Figure 2:
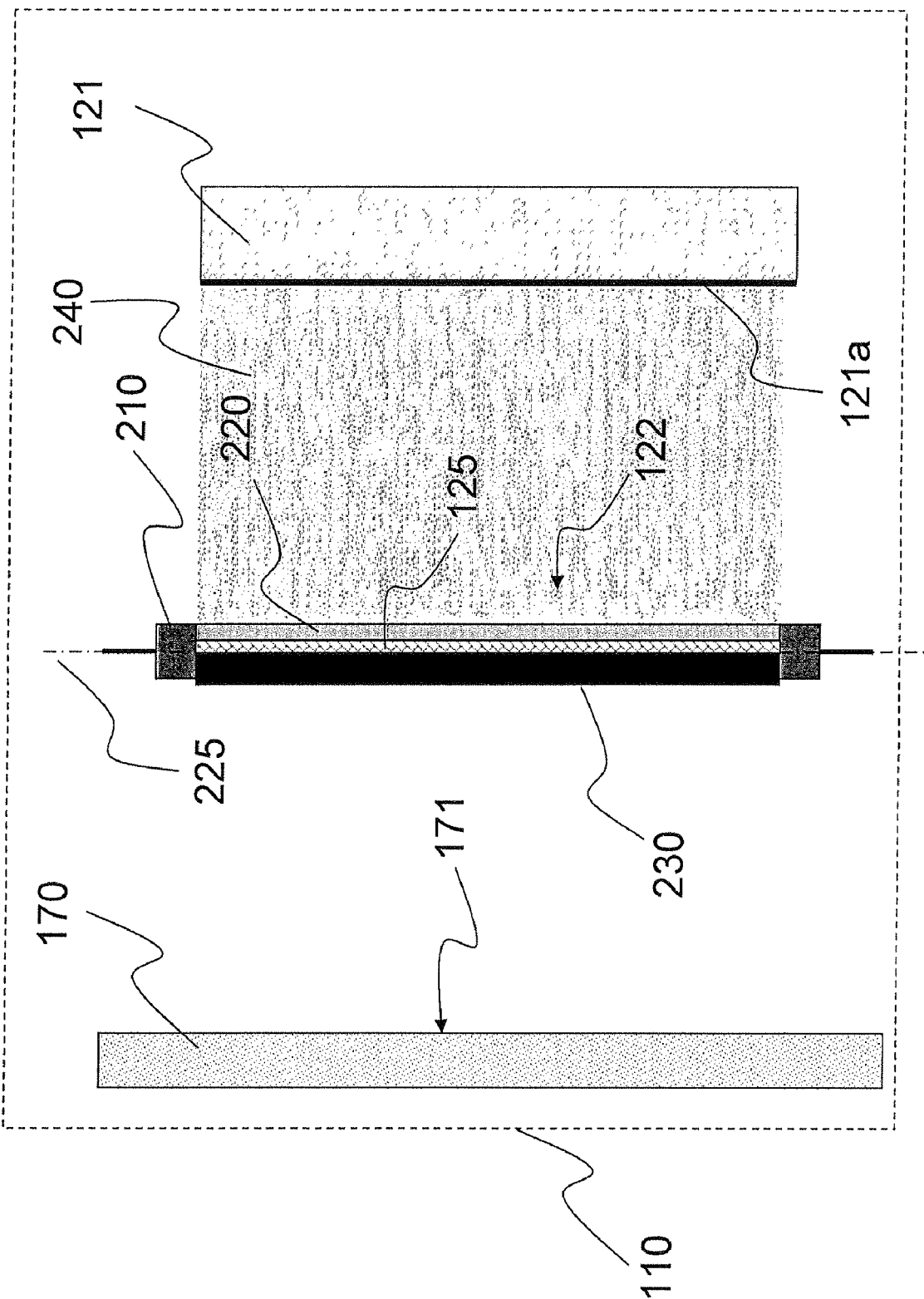
FIG. 2 illustrates an enlarged elevation view of the photocatalytic oxidation subsystem of FIG. 1.

Referring now to FIG. 2, illustrated is an enlarged elevation view of the photocatalytic oxidation subsystem 110 of FIG. 1. For simplicity, only one photocatalytic light bulb 122 is shown. In the presently depicted embodiment, the photocatalytic light bulb 122 is constructed according to the principles of the present invention, and comprises an ultraviolet lamp 210 having a transparent tubular bulb 220 with a longitudinal axis 225, and a light-absorptive barrier 230. Note that the light-absorptive barrier 230 is positioned on a side of the transparent tubular bulb 220 proximate a surface 171 of the system filter 170 and is thus between the ultraviolet lamp 210 and the system air filter 170. For the purposes of this discussion, a light-absorptive barrier is defined as one that primarily absorbs photonic energy rather than one that reflects photonic energy, e.g., at least 51 percent of the photonic energy is absorbed versus not more than 49 percent of the photonic energy is reflected. In the illustrated embodiment, the light-absorptive barrier 230 is applied to an outside of the transparent tubular bulb 220.

In those applications wherein a UV light source is used without benefit of a photocatalytic coating, other components of the HVAC system, e.g., electrical insulation, or other polymers, may be susceptible to damage from UV light. In those cases, the orientation of the UV light source would be such that the absorptive barrier 230 is positioned proximate the susceptible system component.

The electrical circuit 125 of the ultraviolet lamp bulb 210 emits photons 240 within 360° around the longitudinal axis 225. Those photons 240 exiting the bulb 210 on a side opposite the barrier 240 impact the photocatalytic monolith 121 and cause the subsystem 110 to operate as intended to clean the air by oxidizing and removing contaminants. In one embodiment, the absorptive barrier 240 comprises at least a portion of the transparent tubular bulb 220. In one embodiment, the absorptive barrier 240 comprises substantially 50 percent of the surface of the transparent tubular bulb 220. In another embodiment, the absorptive barrier 240 comprises substantially 180° of the circumference of the transparent tubular bulb 220.

Figure 3:
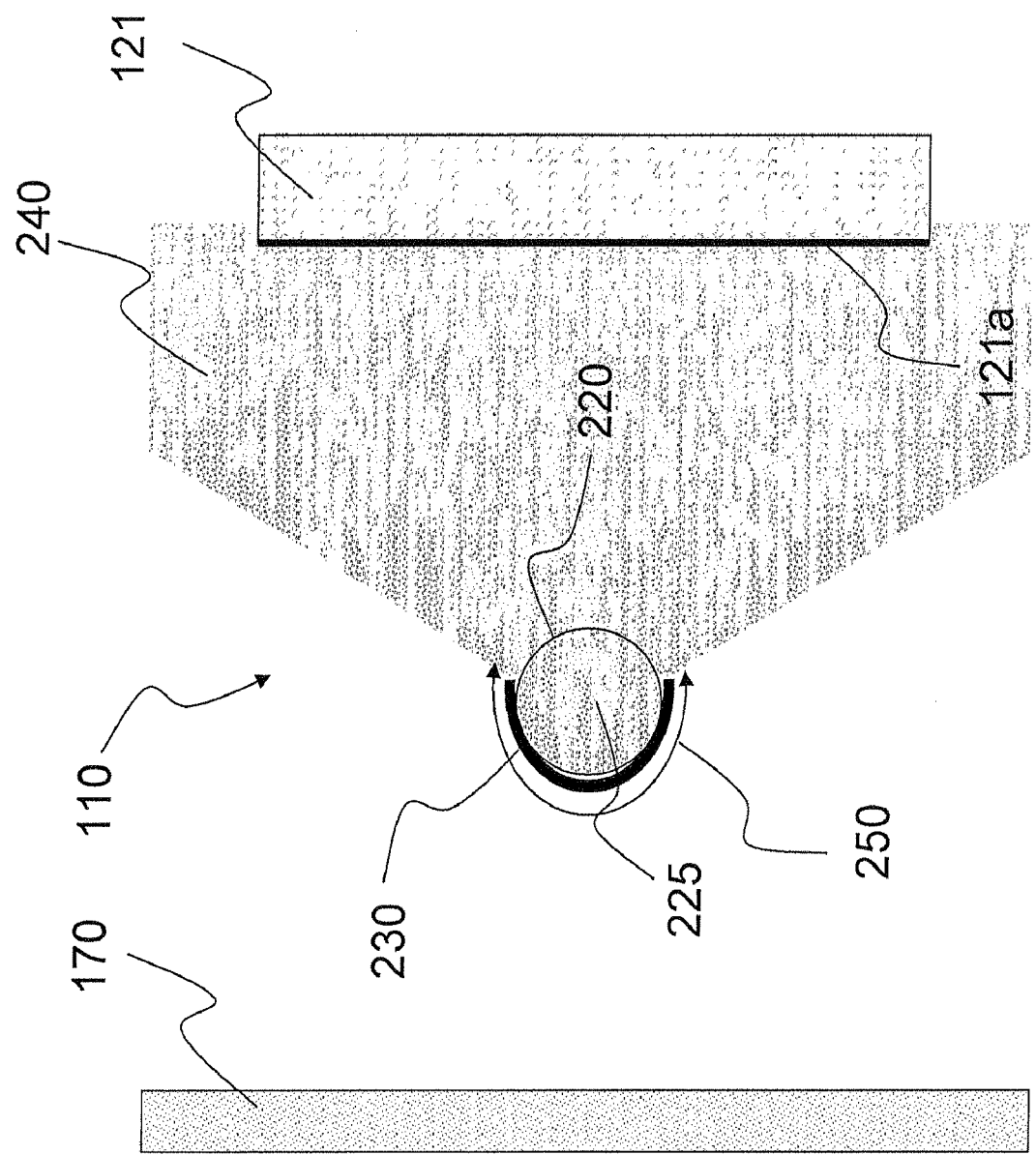
FIG. 3 illustrates a plan view of the photocatalytic oxidation subsystem of FIG. 1.

Referring now to FIG. 3, illustrated is an enlarged plan view of the photocatalytic oxidation subsystem 110 of FIG. 1. In one embodiment, the absorptive barrier 230 comprises a material that absorbs UV light. In a preferred embodiment, the absorptive barrier 230 forms an arc 250 that ranges from about 180° to about 200° of a circumference of the transparent bulb 220. In one embodiment, the absorptive barrier 230 comprises a film applied to an exterior of the transparent tubular bulb 220. In one embodiment, the film 230 comprises a black paint that absorbs the photons 240. The paint 230 may comprise: HiHeat Bar-B-Que Black paint, a product of Rust-Oleum® Corporation of Vernon Hills, Ill. In an alternative embodiment, the paint 230 may comprise a heat-resistant black paint product of Sheffield Bronze Paint Corp. of Cleveland, Ohio titled: Pot Belly Black, Item #906.

In one embodiment, the absorptive barrier 230 may comprise a UV absorptive film 230. The UV absorptive film 230 may comprise UVShield™, a product of CPFilms Inc., of Filedale, Va. UVShield is a clear film that absorbs 99.9% of UVA and UVB manufactured by a patent pending process. Of course, UV light absorbing films may also have a color, i.e. silver, bronze, etc. Thus, UV light transmission is substantially reduced beyond the UV absorptive-covered portion of the transparent tubular bulb 220.

Figure 4:
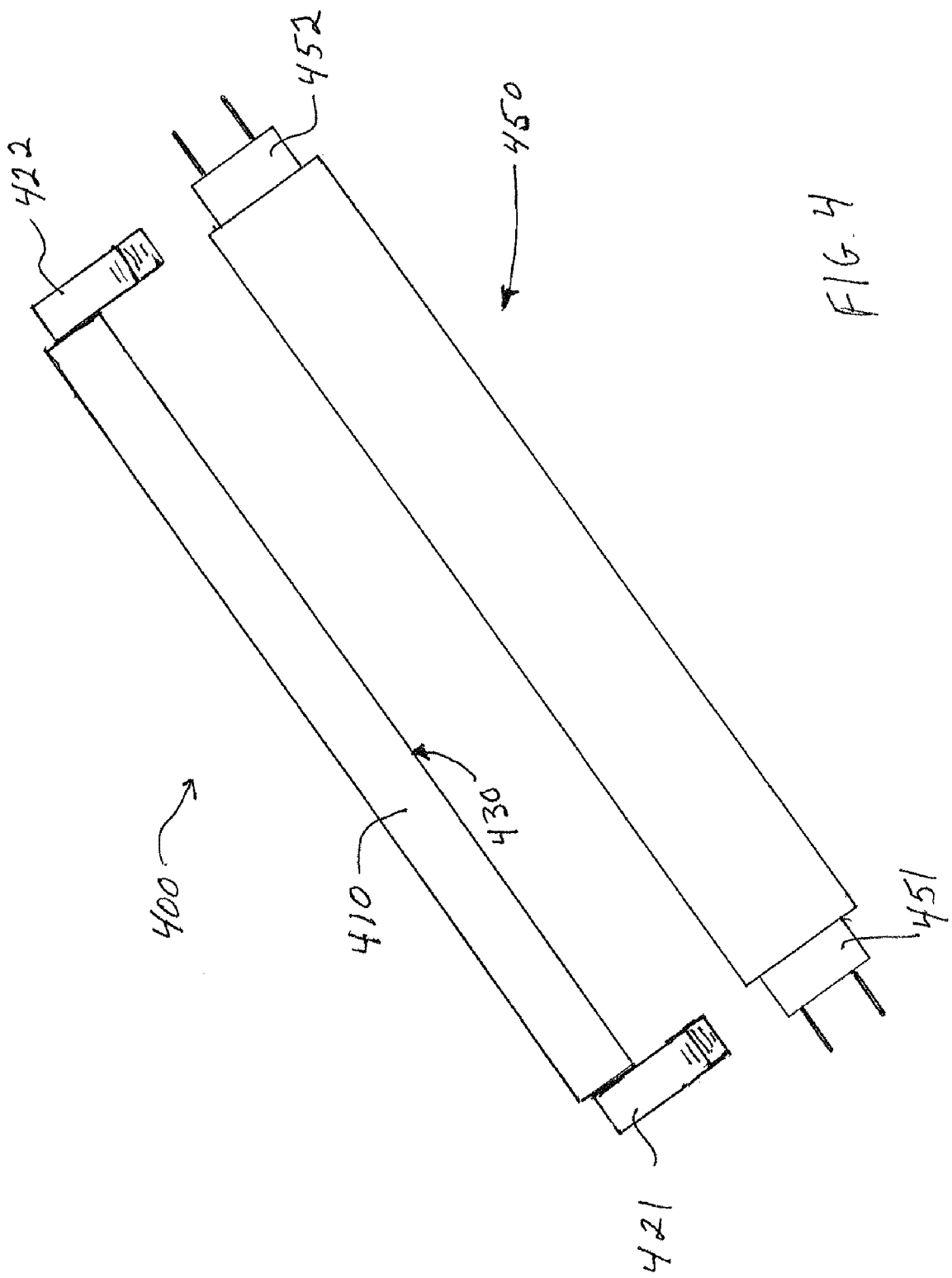
FIG. 4 illustrates an exploded isometric view of an alternative embodiment of a UV absorptive shield and UV light source constructed according to the principles of the present invention.

Referring now to FIG. 4, illustrated is an exploded isometric view of an alternative embodiment of a UV absorptive shield 400 and UV light source 450 constructed according to the principles of the present invention. The UV absorptive shield 400 comprises a rigid semi-circular cover 410, first and second clips 421, 422, and an absorptive layer 430. In a preferred embodiment, the semi-circular cover 410 is sized to fit snugly around the light source 450 which may be a UV lamp as previously described. The absorptive layer 430 may be applied to an inside of the cover 410, or the cover 410 may be integrally molded of UV absorptive material. The first and second clips 421, 422 snap around the ends 451, 452 of the UV lamp 450 in a manner similar to household broom holders, holding the UV absorptive shield 400 to the UV lamp 450. The first and second clips 421, 422 may be made of any suitable material having the requisite spring, e.g., metal, plastic, etc. UV radiation is thus prevented from passing outside of the UV lamp 450 in the portion where the lamp surface is covered with the substantially semi-circular cover 410.

Thus, a light source has been described that prevents UV radiation from impinging on components of a HVAC system, e.g., the system filter, electrical insulation, etc., that could be damaged by the UV radiation.

Although the present invention has been described in detail, those skilled in the pertinent art should understand that they can make various changes, substitutions and alterations herein without departing from the spirit and scope of the invention in its broadest form.

What is claimed is:

1. A heating, ventilating and air conditioning (HVAC) system, comprising:
   an air plenum having an air filter located therein that is susceptible to degradation upon exposure to light;
   a light bulb located within said plenum, said light bulb having a first side proximate said air filter and having a light-absorptive barrier coupled thereto, said light-absorptive barrier configured to reduce light transmission from said light bulb to said air filter to thereby inhibit degradation of said air filter; and
   an air purifier that is light activated, said light bulb being located in said plenum between said air filter and said air purifier, wherein said light bulb has a second side proximate said air purifier, and wherein light emanating from said second side is incident on said air purifier with sufficient intensity to activate said air purifier.

2. The HVAC system as recited in claim 1 wherein said air purifier includes a photocatalytic coating and said light bulb is capable of emitting photonic energy that has a wavelength suitable to activate said photocatalytic coating.

3. The HVAC system as recited in claim 1 wherein said air filter comprises a polymer.

4. The HVAC system as recited in claim 1 wherein said light bulb is capable of emitting photonic energy within an ultraviolet spectrum.

5. The HVAC system as recited in claim 1 wherein said light-absorptive barrier comprises a film coupled to said first side.

6. The HVAC system as recited in claim 1 wherein said light-absorptive barrier comprises a UV absorptive film.

7. The HVAC system as recited in claim 1 wherein said light-absorptive barrier comprises a black paint coupled to said first side.

8. The HVAC system as recited in claim 1 further comprising:
   a snap-on shield wherein said light-absorptive barrier is coupled to said snap-on shield; and
   a clamp couplable to said snap-on shield and configured to couple said snap-on shield to said light bulb.

9. The HVAC system as recited in claim 1 wherein said light-absorptive barrier covers about 50 percent of a surface of said light bulb.

10. The HVAC system as recited in claim 1 wherein said light-absorptive barrier ranges from about 180° to about 200° of a circumference of said light bulb.

11. A heating, ventilating and air conditioning (HVAC) system, comprising:
    a light bulb configured to emit photonic energy; and
    an absorptive barrier coupled to at Least a portion of an outside of said light bulb and configured to substantially reduce transmission of said emitted photonic energy beyond said portion.

12. The HVAC system as recited in claim 11 wherein said photonic energy has a wavelength suitable to activate a photocatalytic coating.

13. The HVAC system as recited in claim 11 wherein said photonic energy has an ultraviolet wavelength.

14. The HVAC system as recited in claim 11 wherein said absorptive barrier comprises a film coupled to said portion.

15. The HVAC system as recited in claim 11 wherein said absorptive barrier comprises a UV absorptive film.

16. The HVAC system as recited in claim 11 wherein said absorptive barrier comprises a black paint coupled to said portion.

17. The HVAC system as recited in claim 11 further comprising:
    a snap-on shield wherein said absorptive barrier is coupled to said snap-on shield; and
    a clamp couplable to said snap-on shield and configured to couple said snap-on shield to said light bulb.

18. The HVAC system as recited in claim 11 wherein said portion is about 50 percent of a surface of said light bulb.

19. The HVAC system as recited in claim 11 wherein said portion ranges from about 180° to about 200° of a circumference of said transparent bulb.

20. A method of manufacturing a heating, ventilating and air conditioning (HVAC) system, comprising:
    providing an air plenum having an air filter located therein that is susceptible to degradation upon exposure to light;
    positioning a light bulb within said plenum, said light bulb having a first side proximate said air filter and having a light-absorptive barrier coupled thereto, said light-absorptive barrier configured to reduce light transmission from said light bulb to said air filter to thereby inhibit degradation of said air filter; and
    locating an air purifier in said plenum that is light activated, said light bulb being located between said air filter and said air purifier, wherein said light bulb has a second side proximate said air purifier, and wherein light emanating from said second side is incident on said air purifier with sufficient intensity to activate said air purifier.

21. The method as recited in claim 20 wherein said light bulb is capable of emitting photonic energy within an ultraviolet spectrum.

22. The method as recited in claim 20 wherein said light-absorptive barrier comprises a film coupled to said first side.

23. The method as recited in claim 20 wherein said light-absorptive barrier comprises a UV absorptive film.

24. The method as recited in claim 20 wherein said light-absorptive barrier comprises a black paint coupled to said first side.

25. The method as recited in claim 20 further comprising:
    coupling said light-absorptive barrier to a snap-on shield; and
    configuring a clamp to couple said snap-on shield to said light bulb.

26. The method as recited in claim 20 wherein said light-absorptive barrier covers about 50 percent of a surface of said light bulb.

27. The method as recited in claim 20 wherein said light-absorptive barrier ranges from about 180° to about 200° of a circumference of said light bulb.

* * * * *